United States Patent [19]

Milner

[11] Patent Number: 5,261,421
[45] Date of Patent: Nov. 16, 1993

[54] GLOVES, THEIR MANUFACTURE AND USE

[75] Inventor: Richard Milner, Bishops Stortford, United Kingdom

[73] Assignee: Smith & Nephew plc, United Kingdom

[21] Appl. No.: 686,171

[22] Filed: Apr. 16, 1991

Related U.S. Application Data

[62] Division of Ser. No. 341,946, Apr. 20, 1989, Pat. No. 5,031,245.

[30] Foreign Application Priority Data

| Apr. 23, 1988 | [GB] | United Kingdom | 8809660 |
| Apr. 23, 1988 | [GB] | United Kingdom | 8809661 |
| Apr. 25, 1988 | [GB] | United Kingdom | 8809709 |

[51] Int. Cl.$^5$ .............................................. A61B 19/00
[52] U.S. Cl. ..................................... 128/898; 128/917
[58] Field of Search ........ 128/846, 917, 918, 897–898; 2/159, 167, 168, 169

[56] References Cited

U.S. PATENT DOCUMENTS

| 3,968,210 | 7/1976 | Schenkel . |
| 4,424,234 | 1/1984 | Alderson et al. . |
| 4,675,347 | 6/1987 | Mochizuki et al. . |
| 4,771,482 | 9/1988 | Shlenker . |
| 4,830,776 | 5/1989 | Thompson . |
| 4,853,978 | 8/1989 | Stockum . |
| 4,919,966 | 4/1990 | Shlenker . |
| 5,031,245 | 7/1991 | Milner . |
| 5,061,106 | 10/1991 | Kent . |
| 5,180,605 | 1/1993 | Milner . |

FOREIGN PATENT DOCUMENTS

| 0141628 | 5/1985 | European Pat. Off. . |
| 0147970 | 7/1985 | European Pat. Off. . |
| 0229862 | 7/1987 | European Pat. Off. . |
| 306389 | 3/1989 | European Pat. Off. . |
| 318258 | 5/1989 | European Pat. Off. . |
| 328421 | 8/1989 | European Pat. Off. . |
| 2215506 | 8/1974 | France . |
| 8605391 | 9/1986 | PCT Int'l Appl. . |
| 8804671 | 6/1988 | PCT Int'l Appl. . |
| 8903860 | 5/1989 | PCT Int'l Appl. . |
| 8904647 | 6/1989 | PCT Int'l Appl. . |
| 219721 | 7/1924 | United Kingdom . |
| 1034112 | 1/1963 | United Kingdom . |
| 1088498 | 10/1967 | United Kingdom . |
| 1099865 | 1/1968 | United Kingdom . |
| 1337617 | 11/1973 | United Kingdom . |
| 1418625 | 12/1975 | United Kingdom . |
| 1421100 | 1/1976 | United Kingdom . |
| 1541155 | 2/1979 | United Kingdom . |

*Primary Examiner*—Lee S. Cohen
*Assistant Examiner*—J. P. Lacyk
*Attorney, Agent, or Firm*—Rosenman & Colin

[57] ABSTRACT

Antimicrobial gloves such as those made of natural rubber latex may be manufactured by incorporating an antimicrobially effective amount of a non-ionic, sparingly water soluble antimicrobial agent, such as 2,4,4'-tricloro-2'-hydroxyphenyl ether, into the glove material prior to forming the glove. The antimicrobial agent may be present in amounts ranging from 0.1 to 10% by weight of the antimicrobial agent. The wearer contacting surface of the glove may also be dusted with a powder containing an antimicrobial effective amount of an antimicrobial agent such as chlorhexidine digluconate. The powder may comprise a complex of chlorhexidine digluconate and cyclodextrin.

3 Claims, No Drawings

GLOVES, THEIR MANUFACTURE AND USE

This is a division of Ser. No. 341,946, filed Apr. 20, 1989, now U.S. Pat. No. 5,031,245.

This invention relates to gloves and more particularly to the type of gloves worn by medical practitioners such as surgeons, nurses and other medical or paramedical personnel, to the manufacture of such gloves and to their use.

Conventionally surgical gloves are manufactured from extremely thin elastomeric materials such as natural or synthetic rubbers. These gloves fit closely and tightly over the users hand. One disadvantage which is experienced with this type of glove is that they are sometimes punctured or ruptured in use. The presence of any small hole such as that caused by a surgical needle or other surgical instrument can result in contamination and infection at the operation site by transfer of bacteria from the inside of the glove to the open wound or to the surgical instruments. Also if body fluids of the patient carry viable bacteria or viruses these may penetrate through a discontinuity in the glove and if they contact broken skin can cause infection of the surgical personnel involved. It has even been suggested that channels can exist in latex gloves which allow viruses to pass through. Although it is the custom for the medical personnel to scrub their hands vigorously with an antibacterial skin cleanser before donning gloves, the anti-infective agent effect may be short lived and infective agents such as bacteria may regrow beneath the gloves in the moist warm environment. If a glove is punctured in use it may not be recognised and the operation is continued allowing a risk of infection.

It has been suggested that a way of protecting the user of a glove is to provide a coating containing an anti-infective agent (see European Patent Publication No.300814). A secure method of protection is required which does not rely upon maintaining the integrity of a coating (during manufacture and use). Such a method has now been discovered.

It has now been found that by using a glove into which a non-ionic sparingly water soluble antimicrobial agent (for example 2,4,4$^1$-trichloro-2$^1$-hydroxydiphenyl ether [triclosan]) has been incorporated, the risk of infection to the patient and the glove wearer is reduced. The level of the antimicrobial agent available on the skin of the wearer is sufficient to inhibit many common bacteria and also to help inhibit certain viruses. It is also believed that such a level would be sufficient to provide an improved barrier to infective agents including certain viruses such as the H.I.V. and Hepatitis B.

Thus in accordance with the invention, there is provided a method for the manufacture of antimicrobial gloves, such as surgeon's or examination gloves including the step of incorporating an effective amount of non-ionic, sparingly water soluble antimicrobial agent into the glove material prior to the glove forming process.

The present invention also provides a antimicrobial glove which contains a non-ionic, sparingly water soluble antimicrobial agent.

The antimicrobial agent is non-ionic at neutral pH values and only sparingly solubele in water. By sparingly water soluble it is meant that the antimicrobial agent has a solubility in water at 20° C. of less than 0.1 gm/liter, preferably less than 0.05 gm/liter.

The gloves may be used as surgeons gloves, as examination gloves or for any other purpose which it is desired to reduce the risk of infection. Aptly the glove is a surgeons glove. Aptly the glove is an examination glove.

The glove material will contain (i.e. within its material as opposed to residing only on its surface) an antimicrobially effective amount of antimicrobial agent. Suitably the glove material may contain from 0.1 to 10% w/w of antimicrobial agent, more suitably 1 to 5% w/w and preferably about 1.0% ww.

The material which forms the gloves can be any one those which are conventionally used for forming gloves especially medical gloves and include natural rubber, polyvinyl chloride and polyurethane. The use of a natural rubber latex to form the glove material is preferred. The use of a non-ionic sparingly soluble antimicrobial agent in a natural rubber latex glove offers a method of overcoming many of the potential problems which could occur with natural rubber latex gloves if they are susceptable to penetration by virus such as those responsible A.I.D.S and Hepatitis B.

From the foregoing it will be appreciated that in a preferred aspect this invention provides a natural rubber latex glove which contains non-ionic, sparingly soluble antimicrobial agent.

The preferred antimicrobial agent is 2,4,4'-trichloro-2'-hydroxydiphenyl ether (triclosan).

Thus in a preferred aspect the present invention provides a natural rubber latex glove which contains 2,4,4'-trichloro-2'-hydroxydiphenyl ether.

These antimicrobial agents are particularly suitable for incorporation into gloves formed from natural rubber latex. It has been observed that natural rubber latices may be coagulated by ionic antimicrobial agent. If articles formed from natural rubber latices are to be treated with such antimicrobial agents, it is after the rubber has been vulcanised that this can be achieved. The nature of the surface of cured rubber articles is such as to be not readily coated or impregnated with for example an antimicrobial agent. Methods of overcoming this problem have included coating the glove with the antimicrobial agent, in a binding agent modifying the rubber surface to make it responsive to binding the antimicrobial agent or by treating the surface with a solvent to cause the rubber to swell and then impregnating with the antimicrobial agent in the same or another solvent and finally removing the solvent. These processes are difficult to carry out and do not give a consistent product. Surprisingly it has been found that non-ionic, sparingly water soluble antimicrobial agents do not coagulate natural rubber latex. This enables the antimicrobial agent to be uniformly mixed with the rubber latex in the fluid pre-cured state which makes manufacture of rubber articles made therefrom easier as it requires no post-cure operations on the article and can also provide a more consistent product. The low solubility of the antimicrobial agent means that it is not removed during the leaching step in the glove manufacturing process yet the antimicrobial agent is found to be effectively released from both the inside and outside of the glove under conditions of which simulate wear.

Suitable non-ionic, sparingly soluble antimicrobial agents include phenol derivatives such as chlorophene, dichloroxylenol, hexachloraphane; diphenyl derivatives, halogenated hydroxy diphenyl derivatives such as diphenyl ethers for example 2,4,4'-trichloro-2'-hydroxy diphenyl ether (triclosan); and agents such as diacetylamino-azotoluene and triclocarban. The preferred antimicrobial agent is triclosan.

The gloves containing antimicrobial agent may be prepared by mixing the required amount of agent with the glove material, for example an dispersion aqueous such as a natural rubber latex. The agent may have been previously formed into a dispersion by mixing with a little of the latex or by mixing with water and dispersing agents. The rest of the latex may be gradually mixed with this dispersion until a homogenous mixture results. The glove is then formed in the usual manner.

Thus, a former may be first dipped into a coagulant solution and allowed to dry. Thereafter the coated glove former is dipped into the latex, removed, dried and immersed in a leaching bath. After drying the glove may then be 'cured'.

In the process described above the antimicrobial agent is distributed through the whole of the glove material so that the agent may be released from both the inside and the outside of the glove. This is generally much preferred, however, it may be desirable for some purposes to have the agent available only on the inside or wearer-contacting surface of the glove. The agent may be present therefore in the material which forms the last coat on the former, that is becomes the inside of the glove when the glove is removed from the former (this process still ensures that the anti-infective agent is contained within the glove).

In an alternative embodiment, the glove former may be precoated with a polymeric matrial such as a polyurethane, and thereafter further coated with the antimicrobial-containing material. In use the coating immediately adjacent the former will become the exterior coating of the glove.

It will be understood that in a preferred aspect this invention provides a thin polymer glove which contains $2,4,4^1$ - trichloro- $2^1$-hydroxydiphenyl ether (triclosan).

Such gloves incorporating a non-ionic sparingly water soluble antimicrobial agent offer the user a high degree of protection from common infecting organisms that might penetrate through any discontinuity in the glove. The use of such gloves can reduce the need for extensive pre-sterilization of the skin as the antibacterial agent is effective in reducing skin flora.

The present invention provides a method of reducing the risk of infection which comprises using thin polymer gloves which contain $2,4,4^1$ - trichloro - $2^1$ - hydroxydiphenyl ether (triclosan). The glove contains an antimicrobially effective amount of triclosan. The triclosan provides protection for 6 to 8 hours.

In another aspect the invention provides a glove which contains a non-ionic, sparingly water soluble antimicrobial agent and which has at least on the inside surface thereof a powder containing antimicrobial agent.

In a preferred aspect the invention provides a glove which contains non-ionic, sparingly water soluble antimicrobial agent and which has at least on the inside surface thereof a powder containing chlorhexidine digluconate.

It is very surprising that chlorhexidine digluconate should be a component of an effective bactericidal dusting powder since it is a hygroscopic or even deliquescent solid and is usually only available as a solution. If used as a solid it would be expected to cause a powder containing it to cake through absorption of water thereby making it ineffective as a dusting powder. However, very surprisingly this is not found to be the case in the dusting powder used in the invention.

In a preferred aspect the present invention provides a glove which contains $2,4,4^1$ - trichloro - $2^1$ - hydroxydiphenyl ether and which has at least on the inside surface thereof a powder containing chlorhexidine digluconate.

Aptly the gloves may be used as surgeons gloves or as examination gloves.

The powder which contains the chlorhexidine digluconate is preferably one of those which is conventionally used as a lubricating or dusting powder for gloves such as examination gloves or surgeons' gloves. Suitable powders include starches especially maize starch and inorganic powders such as calcium carbonate. The powder comprising starch and chlorhexidine digluconate is particularly effective.

The powder will contain an antimicrobially effective amount of chlorhexidine digluconate. The powder may suitably contain from 0.05 to 10% w/w of chlorhexidine digluconate, more suitably may contain from 0.1 to 8% w/w and preferably contains from 0.15 to 6% w/w.

The powder containing an antimicrobially effective amount may be obtained by methods which comprise mixing of the ingredients. Suitable methods include (a) spraying a solution of the appropriate strength of chlorhexidine digluconate onto a fluidised bed of the powder, and (b) mixing a solution of chlorhexidine digluconate with the powder, drying, grinding and sieving the resulting powder to remove large particles or (c) by freeze drying chlorhexidine digluconate and dry mixing with the powder.

The powder containing chlorhexidine digluconate may be coated onto the inside of the glove in the way lubricating powders are conventionally applied. Suitably each glove may have applied to it from 0.2 to 3 gm of the dusting powder and preferably from 0.4 to 1 gm. The glove is then everted and packaged in a conventional manner.

In a second preferred aspect the present invention provides a glove which contains a non-ionic, sparingly water soluble antimicrobial agent and which has at least on the inside surface thereof a powder containing triclosan.

The powder may contain an antimicrobially effective amount of triclosan. The powder may suitably contain from 0.1 to 10% w/w of triclosan, more suitably may contain from 0.5 to 8% w/w and preferably contains about 1% w/w.

The powder containing an antimicrobially effective amount of triclosan may be obtained by methods which comprise mixing of the ingredients. Suitable methods include (a) mixing a solution of triclosan in acetone with the powder, drying, grinding and sieving the resulting powder to remove large particles and (b) mixing the dry powders together.

The powder containing triclosan may be coated onto the inside of the glove incorporating the non-ionic, sparingly water soluble antimicrobial agent such as triclosan itself in the way lubricating powders are conventionally applied. Suitably each glove may have applied to it form 0.1 to 3 gm of the dusting powder and preferably from 0.4 to 1 gm. The glove is then everted and packaged in a conventional manner.

A further aspect of the invention provides a glove which has at least on the inside surface thereof a powder containing a chlorhexidine digluconate-cyclodextrin complex.

The powder may contain an amount of chlorhexidine digluconate-cyclodextrin complex which contains an equivalent amount of chlorhexidine digluconate as described herein before. The preparation of chlorhexidine digluconate-cyclodextrin complex is described hereinafter. In addition to the complex the powder may contain other materials such as starch.

This powder may be applied to a conventional glove in a conventional manner at a level which is similar to that which the chlorhexidine digluconate powder was applied. This powder may also be beneficially applied to gloves incorporating triclosan as hereinbefore described.

A powder may contain an amount of triclosan-cyclodextrin complex which contains an equivalent amount of triclosan when present in a powder. The preparation of triclosan-cyclodextrin complex is described hereinafter.

Aptly the glove forming material is a natural rubber latex.

Suitable non-ionic, sparingly water soluble antimicrobial agent includes those described herein before.

EXAMPLE 1

Preparation of a Glove

Triclosan was incorporated into a natural rubber latex by mixing the triclosan (42 g) with a small quantity of latex to form a paste. The latex paste was gradually diluted with more latex until the required concentration was achieved. The final latex formulation was :

| | |
|---|---|
| Latex (42% solids) | 4858 g |
| Triclosan | 42 g |

A coagulant solution was prepared consisting of:

| | |
|---|---|
| Calcium nitrate | 12.02% |
| Zinc nitrate | 5.29% |
| Talc | 3.85% |
| Lactic acid | 3.85% |
| Ethanol | 67.4 |
| Methanol | 7.5% |

A glove former, preheated to 112° C. was dipped into this solution, removed and air-dried for about 2 minutes. The coated former was then immersed in the pre-vulcanised natural rubber latex containing triclosan. The latex coated former was then withdrawn, air-dried for about 2 minutes and immersed in a leach tank of water at about 70° C. for 2 minutes to extract any water soluble materials. The glove was cured, dusted with talc and stripped from the former.

A sample of the glove material was taken and tested for release of triclosan by preparing an assay plate coated with agar containing the test organism *Staphyloccocus aureus*. Samples of the glove material incorporating triclosan were cut and placed on the surface of the agar. The samples were 1.5 cm squares. After 30 minuts at room temperature the plates were incubated at 37° C. for 24 to 48 hours and the zone of inhibition of growth round the samples measured. An enhanced zone of inhibition as compared to a sample of non-triclosan containing glove material showed effective release of triclosan.

EXAMPLE 2

Preparation of a Glove

A dispersion of triclosan in water (at 40% solids) was formed by ball milling for 5 hours the following mixture:

| | |
|---|---|
| Triclosan | 100 g |
| DARVAN No. 1* | 20 g |
| Ammonium caseinate (10% soln) | 20 g |
| Water | to 250 g |

*sodium salts of polymerised alkyl nephthalene sulphonic acid (20% solution)

This dispersion was mixed with an aqueous rubber latex (solids content 41.5%) in the following proportions:

| | |
|---|---|
| 40% Triclosan dispersion | 8.3 g |
| Latex | to 800 g |

The two components were mixed until a homogeneous mixture was achieved.

A conventional aqueous calcium nitrate-calcium carbonate coagulation solution was prepared.

A glove former, preheated to 112° C. was dipped into the coagulant solution, removed and air-dried for about 1-2 minutes. The coated former was then immersed in the prevulcanised natural rubber latex containing triclosan. The latex coated former was then withdrawn and air dried from 1½ to 2 minutes. The latex coated former was then immersed for 2 minutes in a tank of water heated to about 70° C. to extract any water soluble materials. The glove was cured at 115° C. for about 25 minutes. After cooling the glove was dusted with corn starch powder and stripped from the former.

EXAMPLE 3

Preparation of Dusting Powder

A 0.17% w/w solution of chlorhexidine digluconate in water (25 g) were mixed with maize starch (23.75 g). The resulting mixture was dried in an oven at 70° C. for four hours. The resulting solid mass was ground in a pestle and mortar and then sieved through a 150 μm sieve so that the dusting powder has a granular size of less than 150 μm diameter. The chlorhexidine digluconate solution was prepared by taking a commercially available chlorhexidine gluconate solution (0.927 g) containing 18.54% w/w chlorhexidine digluconate and diluting to 100 g with water.

Preparation of a Glove

Triclosan was incorporated into a natural rubber latex employing the process described in Example 1.

A glove was formed by the process described in Example 1.

The glove was cured, dusted with chlorhexidine digluconate-containing maize starch and stripped from the former.

A sample of the glove material was taken and tested for release of the antibacterial agents using the method described herein before. An enhanced zone of inhibition as compared to a sample of non-antibacterial agent containing glove material showed effecive release of the antibacterial agents.

EXAMPLE 4

Preparation of Dusting Powder

A 5% w/w solution of triclosan in acetone (10 g) were mixed with maize starch (24.5 g). The resulting mixture was dried in an oven at 50° C. for four hours. The resulting solid mass was ground in a pestle and mortar and then sieved through a 150 μm sieve so that the dusting powder has a granular size of less than 150 μm diameter. The triclosan solution was prepared by taking triclosan powder (5 g) and dissolving in acetone (95 g).

Preparation of Glove

A glove of natural rubber latex incorporating triclosan (1%) was prepared as described in Example 2. A glove on the former had the dusting powder applied to it (on what would be its inside surface) using a small fine haired brush. Sufficient powder was applied over the whole surface to prevent the glove sticking to itself, 0.7 g is a suitable amount.

A sample of the glove material to which had been applied the dusting powder was placed in the centre of a plate containing an agar growing medium seeded with *Staphyloccocus aureus*. The plate was incubated and a zone of inhibition of growth of the bacteria around the sample was observed indicating successful release of the antibacterial agent.

EXAMPLE 5

Preparation of Dusting Power

A triclosan-βcyclodextrin complex was prepared as follows:

β-cyclodextrin (18.75 g) was placed in a 3-necked flask together with distilled water (100 ml) and heated with stirring until the cyclodextrin had dissolved. Triclosan (4.34 g) was dissolved in sodium hydroxide solution (20 ml, 1 molar) and was added to the flask over a period of 30 minutes with stirring. Ethanol (30 ml as 3×10 ml aliquots) was added and the reaction mixture heated and stirred for a further 2 hours. The reaction mixture was then allowed to cool with stirring to room temperature. The alkaline solution was treated with hydrochloric acid (0.5 m) until the pH of the solution was 3.5. A white precipitate was separated from the resulting solution by centrifuging. The precipitate was washed with a small volume of water three times, centrifuging between each wash to remove inorganic materials such as solidum chloride. The precipitate was dried at 65° C. in a vacuum oven for 1 hour. The complex comprising the precipitate was then used in the dusting powder. The complex (4.8 g) was mixed with maize starch (45.2 g) in a ball mill. The resulting powder contained 2% w/w of triclosan.

A glove incorporating triclosan was coated with the dusting powder.

A sample of the coated glove material exhibited antibacterial activity through release of triclosan from the glove and dusting powder.

EXAMPLE 6

Preparation of Dusting Power

A chlorhexidine digluconate-βcyclodextrin complex was prepared as follows:

β-cyclodextrin (11.43 g) was placed in a 3-necked flask together with distilled water (75 ml) and heated with stirring until the cyclodextrin had dissolved. Chlorhexidine diglucoate (48.9 g of an 14.48% w/w aqueous solution) was added to the flask over a period of 30 minutes with stirring. After the addition was complete the solution was heated for a further 15 minutes and allowed to cool with stirring to room temperature. The solution was then placed in a refrigerator at 5° C. until precipitation of a white solid was completed. The precipitation was filtered off and dried. The complex comprising the precipitate was then used in the dusting powder. The complex (5.7 g) was mixed with maize starch (44.3 g) in a ball mill. The resulting powder contained 5% w/w of chlorhexidine digluconate.

A glove was coated with the dusting powder.

A sample of the glove material to which had been applied the dusting powder was placed in the centre of a plate containing an agar growing medium seeded with *Staphyloccocus aureus*. The plate was incubated and a zone of inhibition of growth of the bacteria around the sample was observed indicating successful release of the antibacterial agent.

EXAMPLE 7

Preparation of Dusting Powder

A solution of chlorhexidine digluconate is freeze dried to provide solid particles of chlorhexidine digluconate. These particles are mixed with dry maize or calcium carbonate powder in a ball mill to provide a dry powder containing chlorhexidine digluconate.

The dry powder may be applied to the inside surface of a glove incorporated triclosan (1%) prepared by the method described in Example 2.

I claim:

1. A method of providing a hand of a medical glove user with an improved barrier to bacteria and viruses, which comprises fitting over said hand a natural rubber medical glove comprising an antimicrobially effective amount of 2,4,4'-trichloro-2'-hydroxydiphenyl ether within the natural rubber.

2. A method accoridng to claim 1 wherein said natural rubber medical glove contains an amount of 2,4,4'-trichloro-2'-hydroxydiphenyl ether within the natural rubber sufficient to provide an improved barrier to HIV.

3. A method according to claim 1 wherein said natural medical rubber glove contains an amount of 2,4,4'-trichloro-2'-hydroxydipehnyl ether within the natural rubber sufficient to provide an improved barrier to Hepatitis B.

* * * * *